(12) United States Patent
Prakash

(10) Patent No.: US 10,912,897 B2
(45) Date of Patent: Feb. 9, 2021

(54) SINGLE-USE SYRINGE

(71) Applicant: Indumathi Prakash, Sharon, MA (US)

(72) Inventor: Indumathi Prakash, Sharon, MA (US)

(*) Notice: Subject to any disclaimer, the term of this patent is extended or adjusted under 35 U.S.C. 154(b) by 55 days.

(21) Appl. No.: 15/969,249

(22) Filed: May 2, 2018

(65) Prior Publication Data

US 2018/0318525 A1 Nov. 8, 2018

Related U.S. Application Data

(60) Provisional application No. 62/501,718, filed on May 4, 2017.

(51) Int. Cl.
*A61M 5/50* (2006.01)
*A61M 5/31* (2006.01)
*A61M 5/315* (2006.01)

(52) U.S. Cl.
CPC .......... *A61M 5/508* (2013.01); *A61M 5/3134* (2013.01); *A61M 5/31513* (2013.01); *A61M 5/5066* (2013.01); *A61M 5/31511* (2013.01); *A61M 2005/3131* (2013.01); *A61M 2205/0216* (2013.01)

(58) Field of Classification Search
CPC .............. A61M 5/50; A61M 5/508; A61M 2005/3241; A61M 5/3234; A61M 5/5066
See application file for complete search history.

(56) References Cited

U.S. PATENT DOCUMENTS

| | | | | |
|---|---|---|---|---|
| 2,592,381 | A * | 4/1952 | Blackman | A61M 5/31511 604/222 |
| 5,535,746 | A * | 7/1996 | Hoover | A61M 5/14546 600/432 |
| 5,891,092 | A | 4/1999 | Castellano | |
| 6,368,306 | B1 | 4/2002 | Koska | |
| 8,038,656 | B2 * | 10/2011 | Lloyd | A61M 5/31515 604/218 |
| 2008/0319390 | A1 * | 12/2008 | Ying | A61M 5/508 604/110 |

FOREIGN PATENT DOCUMENTS

| | | | | |
|---|---|---|---|---|
| FR | 2650509 A1 * | 2/1991 | | A61M 5/50 |
| RU | 2065757 C1 * | 8/1996 | | A61M 5/50 |
| WO | WO-0141842 A1 * | 6/2001 | | A61M 5/322 |
| WO | WO-2008015529 A2 * | 2/2008 | | A61M 5/5013 |

* cited by examiner

*Primary Examiner* — Nathan R Price
*Assistant Examiner* — Anna E Goldberg-Richmeier
(74) *Attorney, Agent, or Firm* — Fish & Richardson P.C.

(57) ABSTRACT

A single-use medical syringe having a plunger with a sealing element arranged on a distal end of the plunger head to contact the medicament in the syringe body and one or more hollow piercing elements disposed in the interior of the syringe body between a distal surface of the interior and the sealing element of the plunger head, wherein the one or more hollow piercing elements are arranged axially with respect to the syringe and positioned to be driven though the sealing element when the sealing element is driven against the distal surface at the end of the injection operation, wherein, at the end of the injection operation, the one or more hollow piercing elements create a fluid passageway across the plunger head when the one or more hollow piercing elements pierce through the sealing element of the plunger head.

17 Claims, 12 Drawing Sheets

SINGLE-USE SYRINGE

CLAIM OF PRIORITY

This application claims priority under 35 USC § 119(e) to U.S. Provisional Patent Application Ser. No. 62/501,718, filed on May 4, 2017, the entire contents of which are hereby incorporated by reference.

TECHNICAL FIELD

The field of the disclosure relates to syringes, and in particular, a disposable syringe that is improved to make it a smart syringe to auto-disable and to be single-use.

BACKGROUND

In a given year globally, unsafe injections due to reuse of syringes leads to 21 million new HBV cases (32% of all new cases), 2 million new HCV cases (40% of all new cases), and around 260,000 HIV cases (5% of all new HIV cases). Other diseases can also be transmitted through reused injection equipment, e.g. viral hemorrhagic fever, such as Ebola and Marburg viruses, malaria, Zika virus, etc. In addition, 90% of the more than 16 billion injections administered per year are used for therapeutic care. Though these syringes are typically disposable, reuse is not prevented, and therefore a user's decision to refill and reinject with a disposable syringe is the driving factor behind these alarming statistics. However, with proper safeguards within the syringe to disable operation of the syringe after a first use, reuse can be mitigated.

SUMMARY

Certain aspects of the present disclosure relate to a syringe assembly that, after use, prevents reuse by breaching the plunger head during use such that the plunger head can no longer create a differential pressure in the syringe assembly. In some examples, the syringe assembly includes a plunger head having one or more piercing objects, which have a hollow bore, designed to effectively destroy the operability of the plunger head following a first use. For example, at the end of the first use of the syringe, the piercing objects become an integral part of the plunger head. The hollow bore of the piercing objects allows air or fluid flow to pass through the plunger head, which maintains equalized pressure across the plunger head and thereby disables subsequent injections by eliminating the plunger head's ability to drive a fluid from the syringe. Aspects of this disclosure avoid reliance of pressure equalization through the elastic or plastic material by cutting and detaching some material from the elastic seal or diaphragm material of the plunger head. In some instances, with the least possible force, aspects of this disclosure create a smooth insertion of the hollow bore of the piercing object into the plunger head, through which the air or fluid flows across to break the differential pressure. In some aspects of the present disclosure, the piercing objects, which have a hollow bore between a blunt end and a sharp end, provide a fluid passageway across the plunger head when driven through the plunger head at the end of a first use of the syringe assembly. In some instances, the plunger head includes a elastomeric material disposed around a rigid plastic pushing disc, and the piercing objects include an angled cut out of the sharp end, which allows the piercing object to be driven through both the elastomeric and plastic portions of the plunger head. In some instances, the plunger head includes a pushing disc with pre-cut holes around which the elastomeric sealing material is disposed, and the piercing objects are arranged in the plunger head such that they are driven, during a first use of the syringe assembly, through the elastomeric material and through the pre-cut holes in order to avoid a user having to deliver an extra force to drive the piercing objects through the rigid material of the pushing disc. This example design avoids the piercing object having to create a hole by breaching the rigid material, and just pierces the softer sealing material of the plunger head smoothly to ensure that the hollow bore of the piercing object can equalize the pressure across the seal created by the sealing material of the plunger head.

Certain aspects of the present disclosure include transforming a widely used and functionally matured disposable syringe into a single-use syringe by modifying an existing plunger head to be a mounting device for the new piercing objects and thereby achieving the single-use feature after the first use, where the piercing objects are driven through the plunger head. Aspects of this disclosure provide a simple mechanism for modifying a plunger head to enable single use without complex components, and in a manner that requires little material, and can be provided by existing manufacturing facilities of disposable syringes with little or no modification. In some aspects, the piercing objects can be, for example, distal sections of a standard sterilized injection piercing needles. In some instances, the sharp end is formed by an angled cut at the sharp end, a simple cut at the opposite end forms a blunt end for driving the sharp end of the piercing object through the plunger head. Because aspects of the present disclosure enable the piercing objects to smoothly pierce and equalize the differential pressure across the plunger head, which is the fundamental principle of operation of a syringe, the piercing objects render the plunger head unusable for subsequent injections. This aspect of the disclosure provides wide usability, minimizes additional costs, and allows all the functions of matured and widely available disposable syringes to be transformed into a single-use syringe.

One example is a single-use medical syringe having a syringe body adapted to contain a medicament in an interior of the syringe body, the syringe body having a distal end adapted to deliver the medicament to a needle and an open proximal end and a plunger assembly configured to be inserted into the open proximal end of the syringe body. The plunger assembly is movable with respect to the syringe body for driving the medicament from the syringe body through the needle, and the plunger assembly includes a proximal end adapted to be operated by a user of the single-use medical syringe and a distal end arranged to be driven to the distal end of the syringe body during an injection operation. The distal end of the plunger assembly includes a plunger head adapted to sealingly engage an inner surface of the syringe body, and the plunger head includes a sealing element arranged on a distal end of the plunger head to contact the medicament in the syringe body, and one or more hollow piercing elements disposed in the interior of the syringe body between a distal surface of the interior and the sealing element of the plunger head. The one or more hollow piercing elements are arranged axially with respect to the syringe and positioned to be driven through the sealing element when the sealing element is driven against the distal surface at the end of the injection operation. In addition, at the end of the injection operation, the one or more hollow piercing elements create a fluid passageway across the plunger head when the one or more hollow piercing elements pierce through the sealing element of the plunger head.

In some instances, the one or more hollow piercing element include a piercing end and a blunt end opposite the piercing end and a hollow bore extending between the blunt end and the piercing end. The piercing end is arranged closest to the sealing element, and wherein the blunt end is arranged closest to the distal surface, and the hollow bore defines the fluid passageway across the plunger head when the one or more hollow piercing elements pierce through the sealing element of the plunger head.

In some instances, the piercing ends of the one or more hollow piercing objects are disposed in the plunger head prior to the injection operation such that the one or more hollow piercing objects are carried by the plunger head, and, during the injection operation, the blunt ends of the one or more hollow piercing objects contact the distal surface of the interior of the syringe body such that completion of the injection operation drives the piercing ends of the one or more hollow piercing objects through the sealing element of the plunger head to create the fluid passageway across the plunger head.

In some instances, the single-use medical syringe includes a mounting ring disposed in the interior of the syringe body and at the distal end of the interior of the syringe body, the mounting ring includes a distal surface configured to abut the distal surface at the distal end of the interior and a proximal surface configured to abut the sealing element at the end of the injection operation. The one or more hollow piercing objects are carried by the mounting ring.

In some instances, the blunt ends of the one or more hollow piercing objects extend though the mounting ring such that the hollow bores of the one or more hollow piercing objects are exposed at the distal surface of the mounting ring, and the piercing ends of the one or more hollow piercing objects extend proximally towards the plunger head prior to the injection operation, wherein during the injection operation. The sealing element of the plunger head contacts the piercing ends of the one or more hollow piercing objects and completion of the injection operation drives the one or more hollow piercing objects through the sealing element to create the fluid passageway across the plunger head, and the one or more hollow piercing objects retain the mounting ring to the plunger head at the completion of the injection operation.

In some instances, the mounting ring includes a central opening configured to allow the medicament to be driven from the distal end of the syringe body during the injection operation, and the sealing element includes a central protrusion extending distally, the central protrusion being sized and shaped to fit into the central opening of the mounting ring at the end of the injection operation.

In some instances, the needle defines an internal cross-sectional bore area, and wherein a total internal bore area of the one or more hollow piercing objects is larger than the internal bore area of the needle.

In some instances, the sealing element of the plunger head is constructed from an elastomeric sealing material.

In some instances, the sealing element includes a distal surface configured to contact the medicament and a proximal surface, and the plunger head includes a rigid seal holding disc adjacent to the proximal surface of the sealing element.

In some instances, the one or more piercing objects are sized and shaped to pierce though the sealing element, and the seal holding disc at the end of the injection operation to create the fluid passageway though the plunger head.

In some instances, the seal holding disc defines one or more voids arranged to accept the one or more hollow piercing objects at the end of the injection operation.

Another example is a single-use medical syringe having a syringe body adapted to contain a medicament in an interior of the syringe body, the syringe body having a distal end adapted to deliver the medicament and a proximal end, and a plunger disposed in the syringe body, the plunger being movable with respect to the syringe body for driving the medicament from the single-use medical syringe, the plunger arranged to be driven to the distal end of the syringe body during a drug delivery operation. The plunger includes a sealing element arranged on a distal end of the plunger to contact the medicament in the syringe body, and one or more hollow piercing elements disposed in the interior of the syringe body between a distal surface of the interior and the sealing element of the plunger. In addition, the one or more hollow piercing elements are positioned to be driven through the sealing element when the sealing element is driven against the distal surface at the end of the drug delivery operation, and, at the end of the drug delivery operation, the one or more hollow piercing elements create a fluid passageway across the plunger when the one or more hollow piercing elements pierce through the sealing element of the plunger.

In some instances, a proximal end of the plunger includes a plurality of positioning elements configured to rotationally couple the distal end of a plunger stem when the distal end of the plunger stem contacts the plunger in the syringe body for driving the plunger into the syringe during the drug delivery operation.

In some instances, the plurality of positioning elements include positioning fins extending proximally from the plunger head.

In some instances, the single-use medical syringe includes a detachable plunger stem having a distal end configured to contact a proximal end of the plunger and drive the plunger into the syringe body during the drug delivery operation without axially coupling to the plunger, and a proximal end configured to be operated by a user of the single-use medical syringe for applying a force to the plunger.

In some instances, the proximal end of the plunger includes a plurality of positioning elements configured to rotationally couple the distal end of the plunger stem when the distal end of the plunger stem contacts the plunger in the syringe.

In some instances, the distal end of the plunger stem defines a plurality of radial wedges, and the plurality of positioning elements include positioning fins extending proximally from the plunger head that are configured to extend into the radial wedges of the plunger stem when the distal end of the plunger stem contacts the proximal end of the plunger.

The syringe body can be configured to be disposed in a medical device having a drive mechanism for driving the plunger into the syringe body.

In some instances, the syringe body contains a medicament.

Yet another example is a single-use medical syringe having a syringe body adapted to contain a medicament in an interior of the syringe body, the syringe body having a distal end adapted to deliver the medicament to a needle, an open proximal end, and a plunger configured to be inserted into the open proximal end of the syringe body, the plunger having a proximal end adapted to be operated by a user of the single-use medical syringe and a distal end adapted to be driven to the distal end of the syringe body during an injection operation. The distal end of the plunger includes a sealing element arranged to contact the medicament in the syringe body, and one or more hollow piercing elements disposed in the interior of the syringe body between a distal surface of the interior and the sealing element of the plunger. In addition, the one or more hollow piercing elements are positioned to be driven through the sealing element when the sealing element is driven against the distal surface at the end of the injection operation, and, at the end of the injection operation, the one or more hollow piercing elements create a fluid passageway across the plunger when the one or more hollow piercing elements pierce through the sealing element of the plunger.

DETAILED DESCRIPTION

Figure 1:
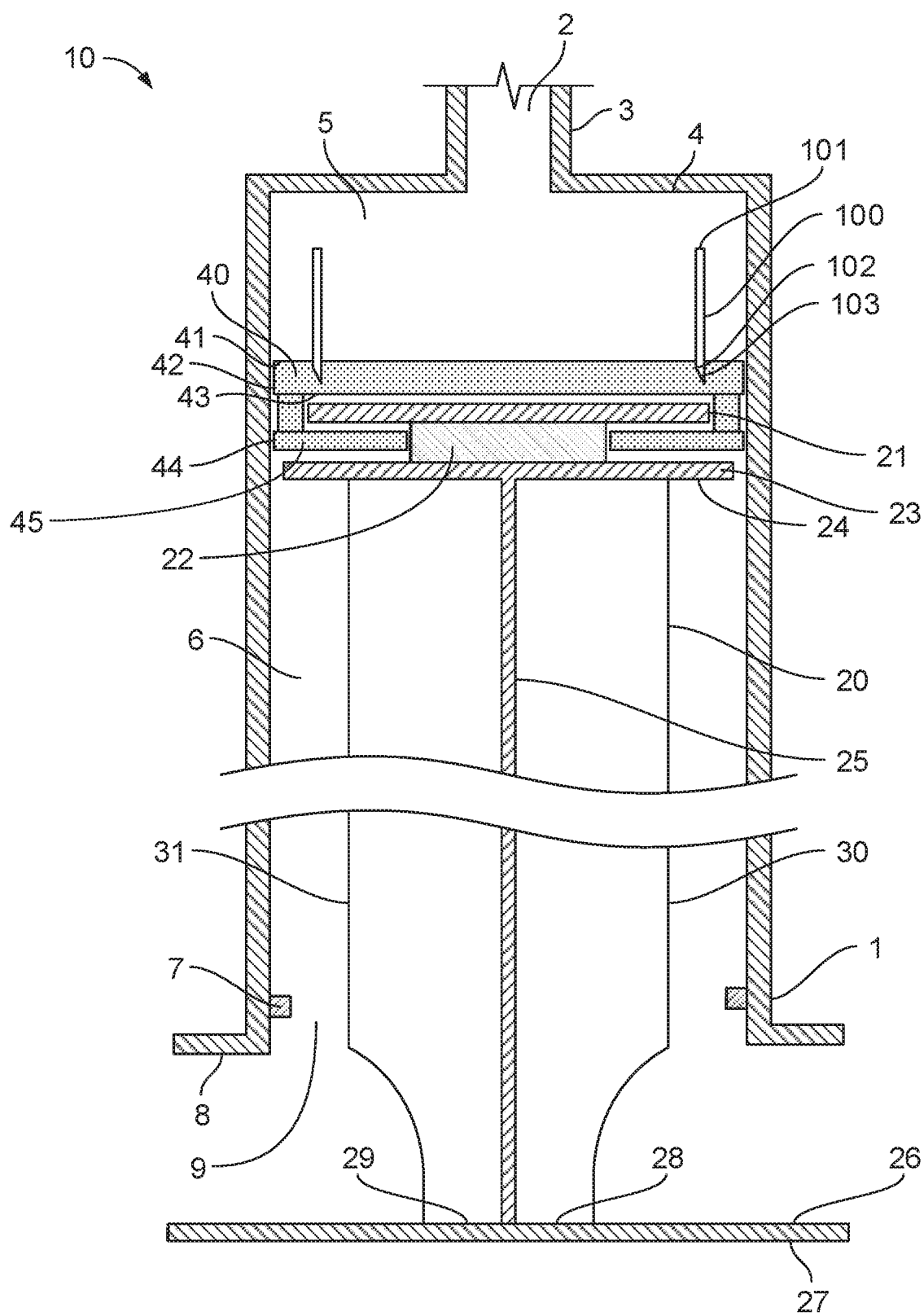
FIG. 1 is a cross-sectional view of a syringe assembly with piercing objects mounted on a plunger head seal before or during first use of the syringe assembly, but prior to completion of the first use.

Traditional disposable syringes have matured in their design with functional components, disposable material choices, and affordability for worldwide application. A notable exception to this maturity is the lack of a widely implemented safeguard to restrict disposable syringes to a single-use. Prior attempts to provide disposable syringes with some single-use functionally have been complicated, often by the addition of a single-use mechanism or structure that obfuscates or modifies the basic syringe functionalities that users and medical practitioners expect from disposable syringes. Many previous single-use concepts require a major change of existing syringe components and methods, which introduces complexities in operation and production, both of which reduce the affordability and adoption. As a result, existing single-use disposable syringes have not provided sufficient effectiveness in combatting improper syringe re-use. Therefore, because worldwide applicability and availability is desired, there is a need for an effective single-use disposable syringe that can be practiced with both minimal loss of functional and the least complexity.

In prior re-use concepts, whenever the fundamental scientific cause of functioning of the device is not eliminated (e.g., the ability to maintain a pressure difference across the plunger head), there is some loophole in the device that removes some functions or becomes complicated. In one such design, as taught in U.S. Pat. No. 6,368,306 Koska, after the plunger head is driven distally into the syringe body at the end of the first use or injection, the plunger head is detached. However, in Koska's design, there is a possibility of a jerking motion while injecting as the plunger head is passed through a groove in the cylinder, which locks the plunger head. In addition, such plunger-retention designs are likely to require some modifications to the injection molding and manufacturing of existing simple disposable syringes without re-use prevision mechanism. While Koska's design could provide for a single-use syringe, it also requires the plunger to be of a special design to avoid accidental snapping of the plunger head during first use or not able to snap after the first use. These modifications create complexities that add to the cost by necessitating unique manufacturing requirements when trying to create a solution for worldwide usages. There are few re-use prevention concepts that have attempted to add single-use functionality by equalizing the pressure, and those existing concepts provide complex components to equalize the pressure across the plunger head to attain the single-use. For example, pressure equalization is taught in U.S. Pat. No. 5,891,092 to Castellano, where the required components are complex. Castellano's design required two seals, and with an additional number of required complex components (e.g., a complex arrangement of piercing objects in an intricately designed distal end of the syringe), the Castellano design is unlikely to be widely implemented as a single-use design invention over the existing mature disposable syringe designs. Moreover, Castellano's components are unique, which requires specialized manufacturing, adding to the cost and deterrent to wide implementation.

Certain aspects of the present disclosure relate to the modification of a basic function of disposable syringes that, after a first use, is disrupted sufficiently by a re-use prevention component to render the syringe unusable for a subsequent injection. This basic function is, for example, the ability of a syringe to maintain a pressure differential across the plunger head while the plunger head is driven into a body of the syringe (e.g., during an injection operation) or out of the body of the syringe (e.g., during a medicament filling operation), which is the fundamental scientific principle required for the functioning of the syringe. Previous re-use concepts have not provided a mechanism to disrupt or equalize the differential pressure across the plunger head assembly after a first use with sufficiently simple implementation and low complexity to allow for widespread adoption.

Many existing designs proving a re-use prevention mechanism by pressure equalization are based on a niche plunger seal and a plunger shape, as opposed to widely available disposable syringes with matured and simple designs of the seals and plunger with minimal material required. Some existing designs attempt to provide differential pressure equalization primarily by creating a hole or rupture through cutting or damaging the seal material, which is often made of an elastomeric material, such as rubber, or neoprene. Cutting or damaging the seal material has disadvantages compared to a simple piercing of the elastomeric material. For example, cutting or damaging the elastomeric seal material requires more force to be applied than piercing and it creates a possibility of pressure not being equalized if the rupture or cut is not sufficient to pass a sufficient amount of air or fluid across the plunger head during a re-use attempt. The elastomeric materials widely used in disposable syringes also require relatively more pressure for cutting and removing part of the material in a way to make a permanent pathway through the material, than a simple piercing. When additional force is required to operate a re-use mechanism at the end of the injection, there exists a possibility of an accidental transfer of that force into an injection needle in the biological body of the patient, resulting in an injury.

Hence, there is a need for a single-use syringe solution through equalization of differential pressure across the plunger head, which attains the single-use to a maximum possible extent, but with a simple component to equalize the pressure across the plunger head. Certain aspects of the present disclosure are able to pierce the elastomeric material of the plunger head seal and provide consistent equalization of the pressure using minimal force from the user. Certain aspects of this disclosure are also implemented with existing and widely available disposable syringes and plunger heads, while maintaining their expected functionality. Aspects of this disclosure provide an affordable re-use prevention mechanism using minimal material and added complexity to the operation of the syringe.

Certain aspects of this disclosure transform the existing disposable syringe into a single-use 'smart' syringe, by adding a re-use prevention mechanism. A typical and widely used disposable syringe contains various components as shown in the drawings in FIG. 1 through FIG. 6, along with additional re-use prevention components. Certain embodiments of this disclosure incorporate a re-use mechanism with piercing objects with a disposable syringe while without reducing the full functionality of the disposable syringe. In some examples, the typical components of widely used and functionally matured disposable syringes function without interruption by the re-use mechanism until the end of a first use, after which the re-use mechanism enforces single-use functionality by rendering the disposable syringe inoperable, as described in more detail below.

A single-use syringe according to aspects of the present invention is illustrated in FIG. 1. FIG. 1 is a cross-sectional view of a syringe assembly 10 with piercing objects 100 mounted on in plunger head seal 40 of a plunger head 24 of a plunger 20 before or during a first use of the syringe assembly 10, but prior to completion of the first use. FIG. 1 illustrates the position of the plunger 20 and the mounted piercing objects 100 before or during the first use of the syringe assembly 10 but prior to completion of the first use. The plunger head seal 40 is intact, as shown.

Figure 2:
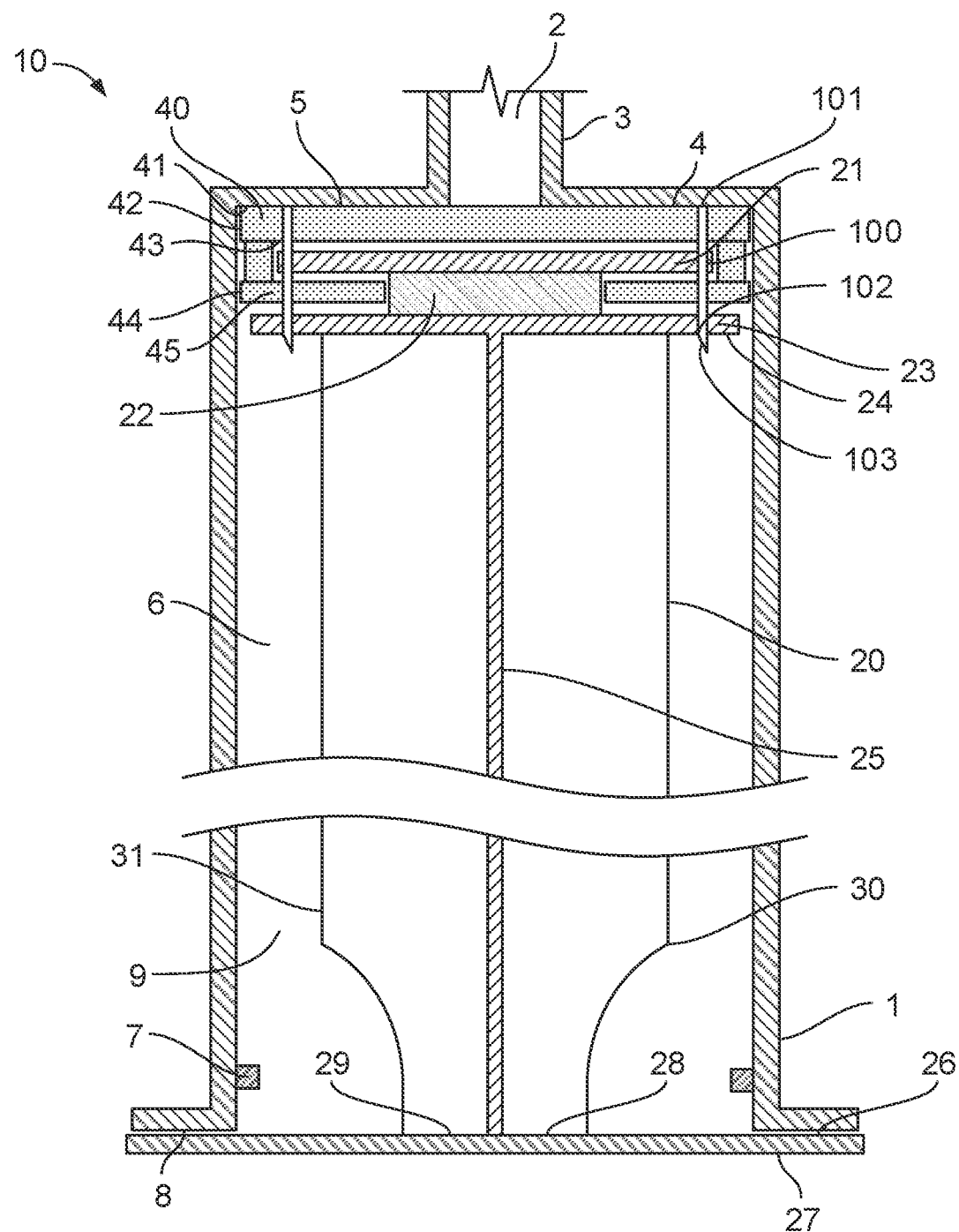
FIG. 2 is a cross-sectional view of the syringe assembly of FIG. 1 showing the plunger head at the distal end of the syringe assembly at the end of first use of the syringe, where the piercing objects have fully pierced the plunger head to equalize the pressure across the plunger head seal.

FIG. 1 shows the syringe assembly with a plunger 20 disposed in a syringe body 1. The plunger head 24 includes a seal holding disc 21 and a seal pushing disc 23 connected to a plunger stem 30 of the plunger 20 by a connector 22. Together, the seal holding disc 21 and the seal pushing disc 23 hold the plunger head seal 40 to the plunger head 24, such that a rear seal 45 of the plunger head seal 40 sits in a groove created between seal holding disc 21 and the seal pushing disc 23. In some instances, the plunger stem 30 is formed from sheets 25, 31 that are fused perpendicular to each other (e.g., forming a 'plus symbol' when seen from the top view as drawn in FIG. 6). While the shape of the plunger stem 30 can vary, in some instances, the plunger stem 30 is sized and shaped to permit the piercing objects to be driven through the plunger head 24 without contacting the plunger stem 30 at the end of a first use of the syringe assembly 10 (as shown in FIG. 2). In some instances, the plunger stem 30 does not interfere with the path of the piercing object 100 such that the hollow bore of the piercing object 100 is not be closed by any part of the plunger stem 30 after a first use of the syringe assembly 10. Continuing to describe the plunger 20, the two perpendicular sheets 25, 31 of the stem 30 are attached a proximal end 29 of the plunger stem 30 to an inner surface 26 of thumb disc 28. In operation, a user or device applies a force to an outer surface 27 of the thumb disc 28 to drive the plunger head 24 into the syringe body 1, and thereby drive the plunger head seal 40 into an interior of the syringe 1 to dispense a medicament during an injection operation, as described in more detail below.

The syringe body 1 includes a distal end 2, where, for example, an injection needle is attached to the syringe body 1. The distal end 2 of the syringe body includes a distal passage 3 configured to pass a medicament from an distal enclosure 5 of the syringe body 1 to the injection needle via the distal passage 3. The distal enclosure 5 is defined as the volume of the interior of the syringe body 1 enclosed by the plunger head seal 40. The distal end 2 also includes a disc surface 4, against which the plunger head seal 40 will contact with an end of an injection operation, whereby the plunger 20 is depressed to drive the plunger head seal 40 distally into the syringe body 1 in order to apply a pressure to a medicament in the distal enclosure 5 and drive the medicament through the distal passage 3 and into the injection needle. The interior volume of the syringe body 1 is split into two areas by the plunger head seal 40, the distal enclosure, as detailed above, where the medicament is held between a distal surface 41 of plunger head seal 40 and the distal end 2, and a proximal region 9 behind a real sealing portion 45 of the plunger head seal 40. The proximal region 9 is open-ended and generally filled with gas or air from the atmosphere in which the syringe assembly 10 is operated. The proximal region 9 of the syringe body 1 contains an interior abutment 7 configured to prevent accidental plunger removal during a pulling of the plunger 20 proximally towards the proximal region 9 for creating suction in the distal enclosure 5 (e.g., for drawing a medicament into the distal enclosure 5 via the injection needle prior to an injection operation). The syringe body 1 also has a flange 8 at a proximal end configured to provide a gripping surface to the user and thus apply force to the plunger 20 relative to the syringe body 1 to vary the differential pressure across the plunger head seal 40, in order to vary the volume of the distal enclosure 5. In some instances, the syringe body 1 is constructed from a semi-transparent or transparent plastic material, with which the medicament in the distal enclosure 5 can be viewed and measured against graduation marks on the syringe body 1.

Returning to the plunger head 24, the distal surface 41 of the plunger head seal 40 is configured to be in contact with a medicament distal enclosure 5. A front side contact surface 42 and a rear side contact surface 44 of the plunger head seal 40 are in contact with an inner surface of the syringe body 1 to create a seal between the plunger head 24 and the syringe body 1 to contain seal the distal enclosure 5 such that a pressure differential can be maintained across the plunger head 24 (e.g., a pressure difference between the distal enclosure 5 and the proximal region 9). The pressure differential is created by a user moving the plunger head 24 into the syringe 1, either proximally (e.g., to draw a medicament into the syringe body 1), or distally (e.g., to drive the medicament from the syringe body 1). In some instances, there is a non-contact area between the front 42 and rear 44 side contact surfaces allowing the plunger head seal 40 to flex like a bellow while the plunger head 24 moves in the syringe body 1. In some instances, the plunger head seal 40 is constructed from an elastomeric material. In some instances, the plunger head seal 40 and rear seal 45 are constructed from a single piece made of, for example, an elastomeric material such as rubber, neoprene, etc.

Continuing to refer to FIG. 1, the piercing objects 100 are shown mounted on the plunger head 24 before the first use of the syringe assembly 10, though other initial configurations are described or more detail below. The piercing objects 100, which may be, for example, injection or body piercing needles, have a blunt end 101 and sharp end 103 opposite the blunt end 101, and a hollow bore hollow bore extending through the piercing object 100 from the blunt end 101 to the sharp end. The sharp end 103 of the piercing objects may be, in some instances, formed by an angled cut, forming a hollow bore ending 102 prior to the tip of the sharp end 103. The hollow bore provides a fluid passageway through the hollow bore of the piercing object 100. In the configuration shown in FIG. 1, the sharp end 103 of the piercing objects are mounted in the plunger head seal 40 by piercing the distal surface 41 and being driven proximally a small distance into the plunger head seal 40. Hence, during the initial mounting, without an additional mounting component, the plunger head seal 40 acts as a mounting component. Note that the sharp ends 103 are not inserted beyond a proximal surface 43 of the plunger head seal 40 in order to maintain the integrity of the plunger head seal 40 during the first injection operation of the syringe assembly 10. The piercing objects 100 enable fluid or air to across the plunger head seal 40 only once the sharp end 103 has breached either the proximal surface 43 or the entirety of the rear seal 45.

The position of the plunger head 24 and piercing objects 100, as shown in FIG. 1 where the distal enclosure 5 may be filled with a medicament prior to a first injection operation syringe assembly 10, signifies that the medicament has not been fully injected out through the distal passage 3. Thus, following the configuration of FIG. 1, either the plunger 20 is pulled away from the distal enclosure 5 to intake medicament through the distal passage 3 due to the suction created in the distal enclosure 5, or the plunger 20 is driven distally to create a pressure in distal enclosure 5 to drive the medicament through the distal passage 3.

In operation, with a medicament contained in the distal enclosure 5, a user or device applies a force to the outer surface 27 of the thumb disc 28 to drive the plunger head 24 distally into the syringe body 1. The distal movement of the plunger head 24 creates an increase in pressure on the distal surface 41 of the plunger head seal 40, which is maintained by the integrity of the plunger head seal 40. The increase in pressure on the distal surface 41 drives the medicament from the distal enclosure 5 and, as the medicament leaves the distal enclosure 5, the plunger head 24 is driven distally into the syringe body 1. This is referred to as a first injection operation. As the first injection operation continues, and the distal surface 41 of the plunger head seal 40 is driven towards the disc surface 4 of the syringe body 1, the blunt end 101 of the piercing objects contacts the disc surface 4. Thereafter, continued distal movement of the plunger head 24 causes the sharp end 103 of the piercing objects to be driven through the plunger head seal 40, followed by hollow bore ending 102, until the hollow bore 104 of the piercing object 100 provides a flow passageway through the plunger head seal 40 (either from the distal surface 41 to the proximal surface 43 or continuing through the entirety of the rear seal 45). In some instances, the angled cut of the cylindrical shape between the sharp end 103 and the sharp side hollow bore ending 102 allows the piercing objects 100 to be driven through both the material of the plunger head seal 40 and the more rigid material (e.g., plastic) of the seal holding disc 21 and the seal pushing disc 23. In other instances, the seal holding disc 21 and the seal pushing disc 23 are shaped to have voids in the region where the piercing objects 100 would pass, thus enabling the piercing objects to only be driven through the material of the plunger head seal 40 in order to minimize extra force required to drive the piercing objects 100 into the plunger head seal 40 at the end of the first injection operation, as shown in FIG. 2.

FIG. 2 is a cross-sectional view of the syringe assembly of FIG. 1 showing the plunger head 24 at the distal end 2 of the syringe assembly 10 at the end of a first use of the syringe (e.g., the first injection operation), where the piercing objects 100 fully pierce the plunger head seal 40 and thereby prevent a subsequent pressure differential from being created across the plunger head seal 40 during any subsequent movement of the plunger head 24 in the syringe body 1. At the end of the first injection operation, when the blunt ends 101 of the piercing objects 100 are pushed against the disc surface 4 of the syringe body 1, the sharp ends 103 of the piercing objects 100 are driven into the plunger head seal 40. Prior to the completion of the first injection operation, the blunt ends 101 of the piercing objects 100 contact the distal disc surface 4 and start experiencing a reactive force from the plunger head 24. Subsequently, the piercing objects 100 are pushed gradually into the plunger head front seal 40, then through (or past) the seal holding disc 21, rear seal 45, and finally the seal pushing disc 23, until the piercing objects' 100 hollow bore is fully passed through the plunger head 24. Fluid or air can now easily pass through the hollow bores thus equalizing the pressure between the distal enclosure 5 and the proximal region 9, rendering the syringe assembly 10 inoperable for a second injection operation.

Continuing to refer to FIG. 2, in some instances, and, as shown, the piercing objects are driven through the material of the seal holding disc 21, the rear seal 45, and the seal pushing disc 23. This configuration ensures that the hollow bore from the blunt end 101 to the sharp side 103 is fully pierced through all the components of the plunger head 24 and the pressure equalized between the distal enclosure 5 and the proximal region 9. The length of the piercing objects 100 is sufficient to have the hollow bore extend from the blunt end 101 flush with the distal surface 41 and the sharp side hollow bore ending 102 projected out of the plunger seal pushing disc 23. However, in some instances, the seal pushing disc 23 defines a void above the location of the piercing objects 100, enabling the piercing objects to only need to pierce the rear seal 45 to completely breach of the plunger head seal 40. In other instances, the seal holding disc 21, the seal pushing disc 23, and the rear seal 45 define voids in the path of the piercing objects, such that the piercing objects only need to breach the plunger head seal 40 between the distal surface 41 and the proximal surface 43 in order to breach the plunger head seal 40.

At the end of the first injection operation (e.g., the first use), when the piercing objects 100 are in a fully pierced position, as shown in FIG. 2, fluid or air can pass through the piercing objects 100 from the distal surface 41 and the plunger seal holding disc 21, thus breaking the differential pressure across this plunger head assembly. Hence, after the first injection operation, and during a second or further use of the syringe, as in FIG. 3, the hollow bore of the piercing objects 100 prevents any suction to the fluid from the syringes' distal end 2 through any sort of syringe needle that could be mounted. Thus, single-use is established.

Figure 3:
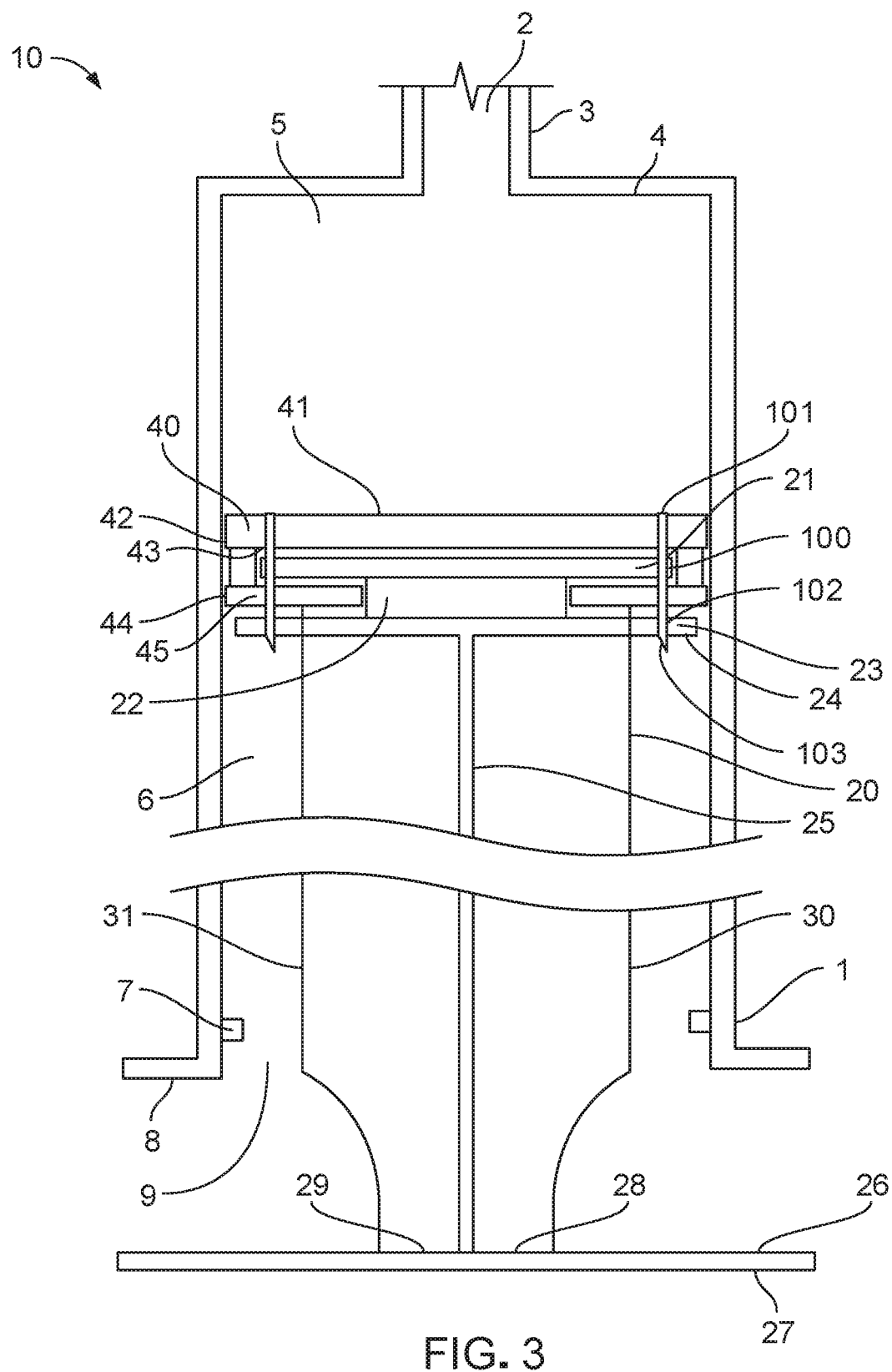
FIG. 3 is a cross-section view of the syringe assembly of FIG. 1, showing the plunger pulled back from the distal end and the piercing objects in a fully pierced position through the plunger head.

FIG. 3 is a cross-section view of the syringe assembly of FIG. 1, showing the plunger 20 pulled back from the distal end 2 of the syringe body 1 after a first injection operation. The piercing objects 100 are in a fully pierced position through the plunger head seal 40. FIG. 3 illustrates a second or any further usage of the syringe assembly 10 after the end of first injection operation, and demonstrates the attaining of the single-use syringe functionality. The condition of the syringe assembly 10 in FIG. 3 illustrates this single-use condition, where air from the distal enclosure 5 flows to the proximal region 9 when the plunger and its head assembly are moved forward towards the distal end 4 and in the reverse flow when moved away from the distal end 2. Therefore, if the plunger 20 is pulled back from the distal end 2 of the syringe body 1, a negative pressure in the distal enclosure 5 sufficient to draw a medicament into the distal enclosure through the distal passage 3 of the syringe body 1 is not achieved. Similarly, if the plunger 20 is driven distally, the plunger head seal 40 cannot create a pressure in the distal enclosure 5 sufficient to drive a medicament through the distal passage 3. Therefore, the syringe assembly 10 is rendered inoperable after the first injection operation in the configuration shown in FIG. 3. Hence, the fundamental principle behind the ability to conduct an injection is eliminated, thus ensuring single-use.

FIG. 3 shows the position of the plunger head assembly in the middle of the cylinder with the piercing objects 100 pierced into the plunger head seal assembly from the plunger head front seal 40 through the plunger head seal holding disc 21. This means essentially, the piercing objects 100 are part of the plunger head seal assembly.

Figure 4:
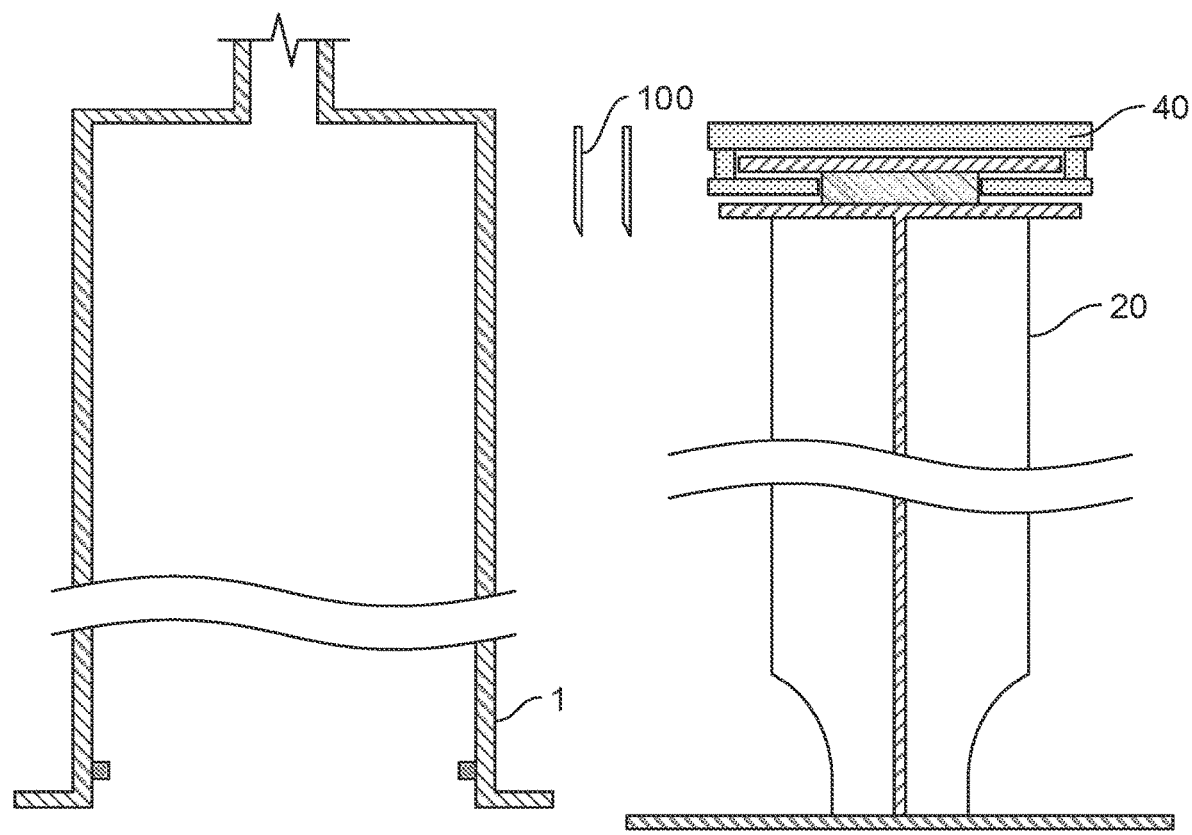
FIG. 4 is a cross-sectional view of different components of the syringe assembly and the piercing objects prior to assembling.

FIG. 4 is a cross-sectional view of different components of the syringe assembly and the piercing objects prior to assembling. FIG. 4 illustrates the basic structure of the syringe body 1, piercing objects 100, plunger 20, and plunger head seal 40 prior to mounting the piercing objects 100 into the plunger head seal 40 and prior to disposing the plunger 20 and plunger head seal 40 into the syringe body 1.

Figures 5A, 5B:
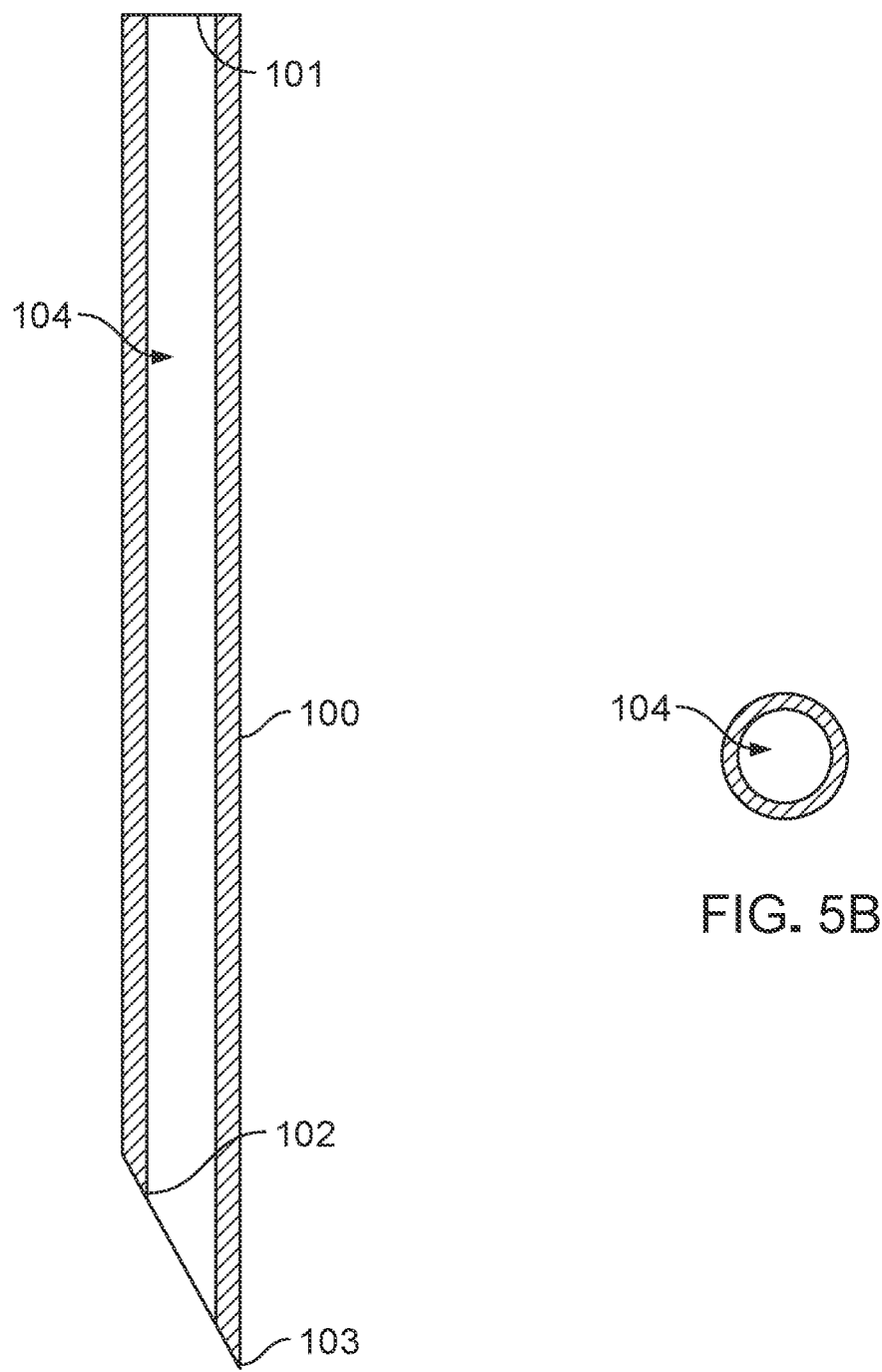
FIGS. 5A and B are cross-sectional views of the piercing object of FIG. 1

FIGS. 5A and 5B are cross-sectional views a piercing object 100, having a blunt end 101, a sharp end 103, a hollow bore ending 102, and a fluid passageway defined by the hollow bore 104.

Figure 6:
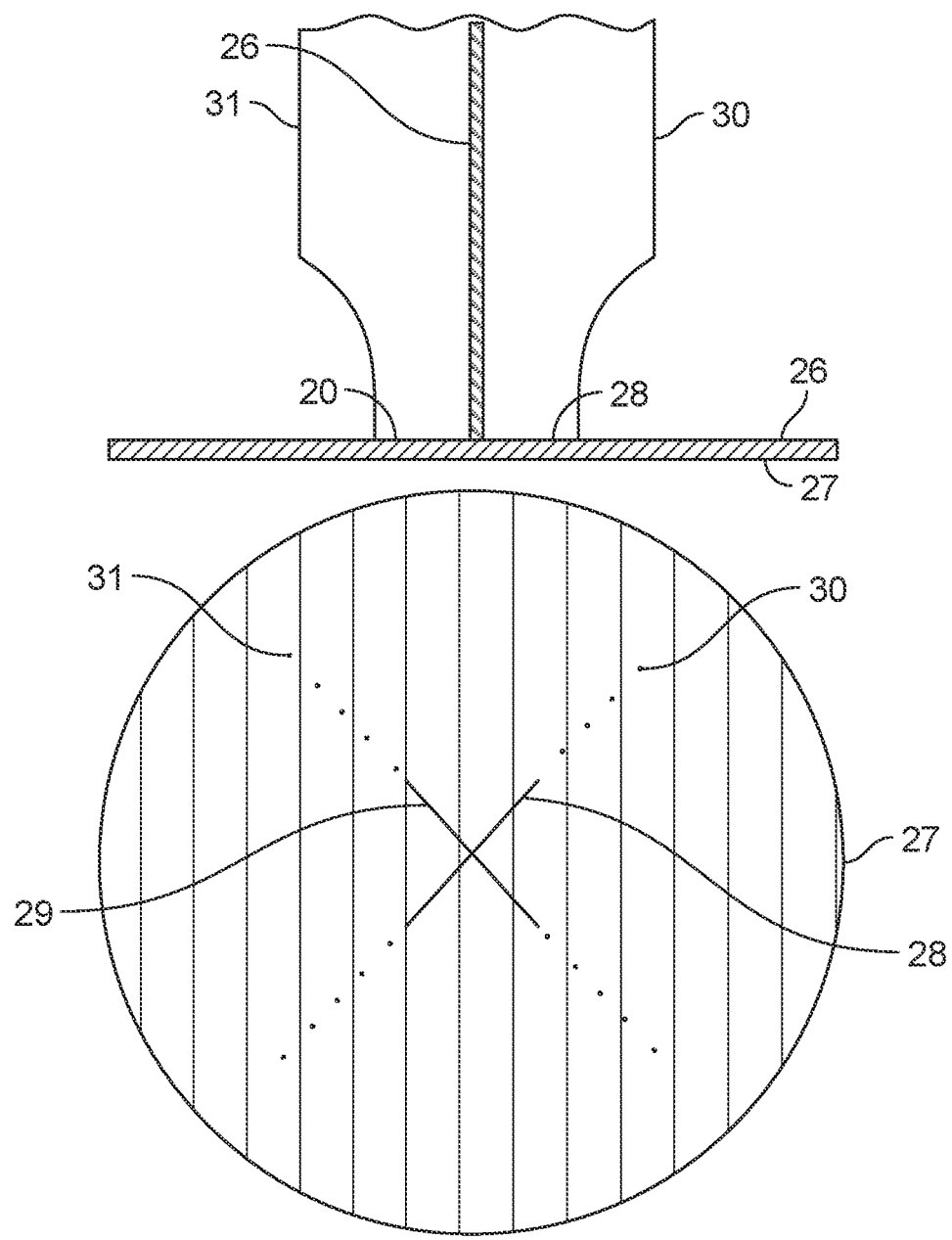
FIG. 6 is a cross-sectional view and end view of the plunger showing the orientation and arrangement of the plunger stem as it is attached to the plunger end disc.

FIG. 6 is a cross-sectional view and end view of the plunger showing the orientation and arrangement of the plunger stem 30 as it is attached to the thumb disc 28.

In certain aspects of the re-use prevention mechanism of this disclosure, as detailed above with respect to FIG. 1-6, the piercing objects 100 mounted on the plunger head 40 provide for an equalizing of differential pressure across the plunger head seal 40 after a first injection operation of the syringe assembly 10. In this configuration, the syringe assembly 10 is a single-use syringe. The following are steps that illustrate the operational transformation from traditional syringe to single-use, as provided by the piercing objects 100. In this example, the piercing objects 100 mounted on the distal surface 41 of the plunger head seal 40 are the re-use prevention mechanism and there is no separate mounting component required for this configuration. However, other configurations of the re-use prevention mechanism are discussed below.

In some instances, the hollow bore of the piercing objects 100 and the number of such piercing objects required is dependent upon a cross-sectional area of the hollow bore required to at least exceed the cross-section area of the hollow bore of the injecting needle that would be mounted on the distal end 2 of the syringe. For a certain embodiment with an injecting needle of 22Q two such 22G piercing needles as piercing objects 100 would suffice. The tensile strength of the piercing object 100 in this case is the exact same as of the injecting needle and can use the standard facilities that manufacture the injecting needle or body piercing needles to cut to a required length without any constriction affecting the hollow bore. Injection or body piercing needles have the same shape required for the piercing object 100 illustrated in this disclosure and so can function as the piercing object with a simple cut to the required length using available manufacturing facilities. In some instances, the sharp end 103 of the piercing objects will not cut the elastic material of the plunger head seal 40, but instead will create a hollow pathway gradually when the main body between the sharp side hollow bore ending 102 and the blunt end 101 gets through the elastic or plastic material of plunger head seal 40 and its holding disc 21. Thus, the force required is of the minimum to pierce through and equalize the pressure.

Although the piercing objects designed in this invention is diagramed with a piercing needle as a particular example, aspects of the present disclosure work with any shape of piercing objects. In some instances, at atmospheric temperature, the hollow bore flow of total air volume of all the piercing objects 100 mounted anywhere on the plunger head assembly, from the plunger head seal 40 to seal pushing disc 23, should be equal or more than the flow of air volume of the injecting needle mounted on the distal end 2 of the syringe. The material of the piercing object can be sterilized can be cut to the length necessary, and have tensile strength sufficient to prevent bending while piercing the material of the plunger seal 40 and, in some instances, one or both of the seal holding disc 21 and the seal pushing disc 23. After piercing the plunger head seal 40, the piercing objects 100 create a fluid passage to equalize the pressure across the plunger head seal 40 without cutting or removing any material from plunger head seal 40.

In general, the embodiments can be manufactured using any type of syringe bodies 1 and plungers 20, any capacity and sizes, any similar compatible materials mentioned and for any medicinal or other single-use usage needs. Also, though an example embodiment is provided in the drawings and descriptions related to the piercing objects, other types of piercing object embodiments are covered in this invention where the hollow pathways of the piercing objects, after piercing, allow for air to flow and equalize the pressure across the seal. Though the foregoing description and drawings cover certain embodiments, it is also understood that there could be other embodiments or modifications made without deviating from the spirit thereof. The presently disclosed embodiments are therefore to be considered in all respects as illustrative and not restrictive. The scope of the invention, rather than the foregoing description, with all the changes which come within the meaning and range of equivalency are therefore intended to be embraced.

Figure 7A:
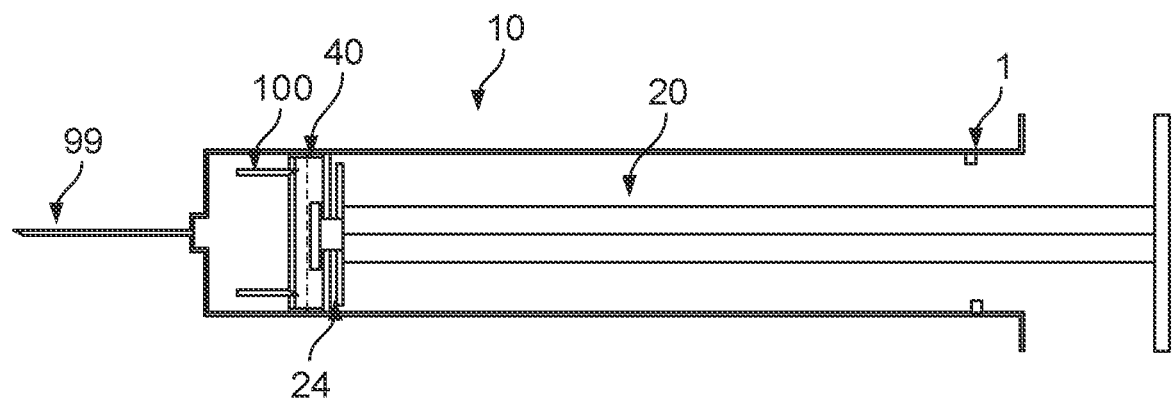
FIGS. 7A-7C are illustrations of different mounting configurations for the piercing objects.
Figure 7B:
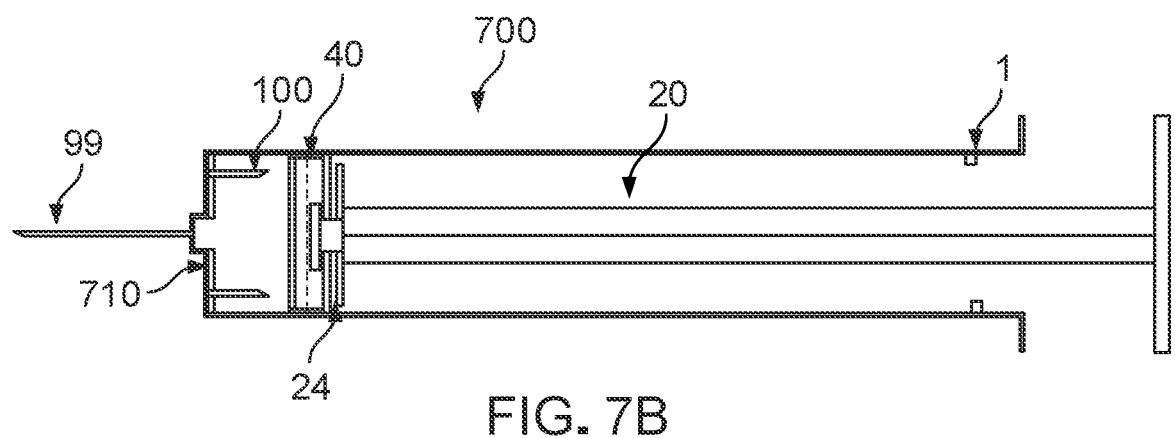
Figure 7C:
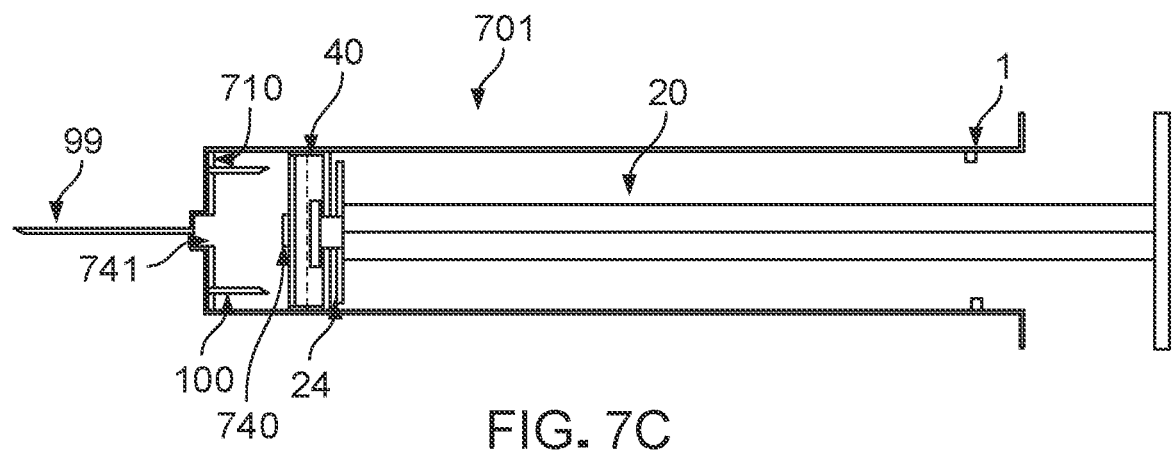

FIGS. 7A-7C are illustrations of different mounting configurations for the piercing objects. FIG. 7A shows the syringe assembly 10 of FIG. 1, in a pre-injection configuration. The syringe assembly 10 includes a needle 99 attached to the distal end of the syringe body 1, and a plunger 20 disposed in the syringe body 1 with a plunger head 24 having a plunger head seal 40. The plunger head seal 40 includes two hollow piercing objects disposed in the plunger head seal 40, as discussed above. FIG. 7B illustrates a syringe assembly 700 aspect of the disclosure having a mounting ring 710 holding the piercing objects 100 at the distal end of the syringe body 1. In operation, the mounting ring 710 is positioned in the syringe body 1 such that the plunger head 24 being driven distally to the distal end of the syringe body 1 during the completion of a first injection operation causes the piercing objects 100 to contact the plunger head seal 40 and be driven through the plunger head seal 40 as the distal surface 41 (shown in FIG. 1) of the plunger head seal 40 is driven against a proximal side of the mounting ring 710. In some instances, the mounting ring 710 carries the piercing objects 100 with their blunt ends 101 extending through the mounting ring to abut the disc surface 4 of the syringe body 1 with the hollow bore 104 being open to the distal face of the mounting ring 710. In operation, at the end of the first injection operation, the piercing objects 100 being driven through the plunger head seal 40 retains the mounting ring 710 against the plunger head seal 40, as discussed i-s in more detail below.

FIG. 7C shows a syringe assembly 701 with the mounting ring 710 of FIG. 7B, with a protrusion 740 on the plunger head seal 40 being configured to mate with a central opening 741 of the mounting ring 710 at the completion of the first injection operation such that any medicament remaining in the central opening 741 is driven from the syringe body 1 by the protrusion mating with the central opening 741.

Figure 8A:
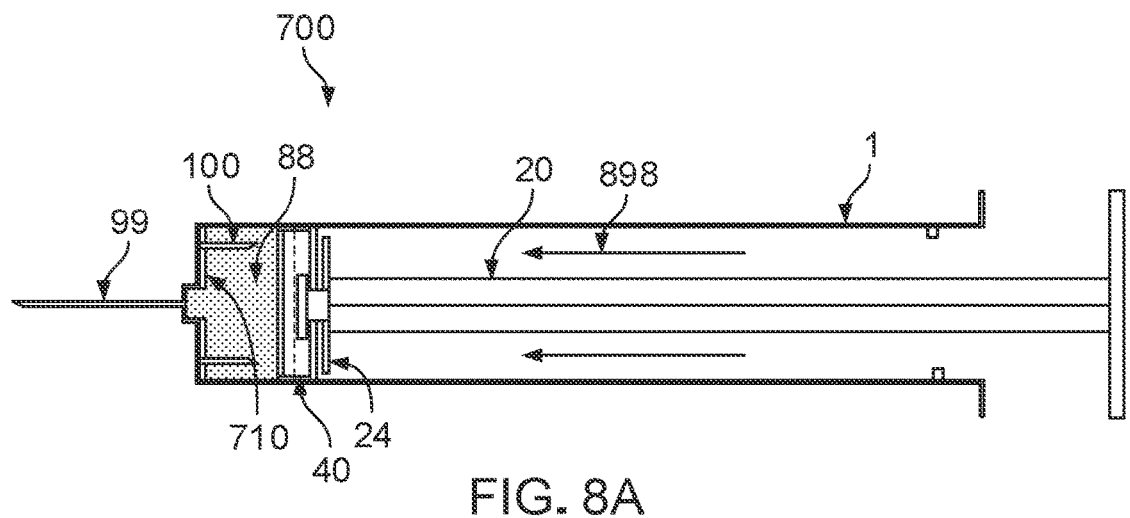
FIGS. 8A and 8B are illustrations of the operation of the mounting configuration of FIG. 7B.
Figure 8B:
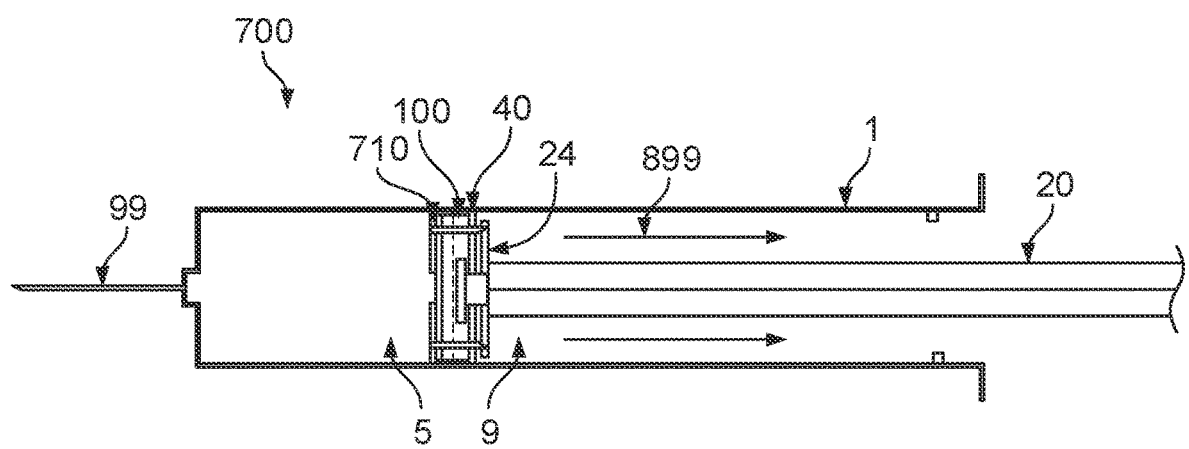

FIGS. 8A and 8B are illustrations of the operation of the mounting configuration of FIG. 7B. FIG. 8A shows the syringe assembly 700 of FIG. 7B having a medicament 88 in the distal enclosure 5 of the syringe 1, along with the mounting ring 710. In operation, the plunger 20 is driven distally (indicated by arrow 898) to drive the medicament 88 through the needle 99 until the distal surface 41 (shown in FIG. 1) of the plunger head seal 40 abuts the proximal face of the mounting ring 710, as shown in FIG. 8B. FIG. 8B shows a proximal movement (indicated by arrow 899) of the plunger 20 after a first injection operation. The piercing objects 100 are driven through the plunger head 40 and equalize the pressure between the distal enclosure 5 and the proximal region 9 as the plunger head 24 moves distally. In addition, the piercing objects 100 retain the mounting ring 710 against the plunger head seal 40.

Figure 9A:
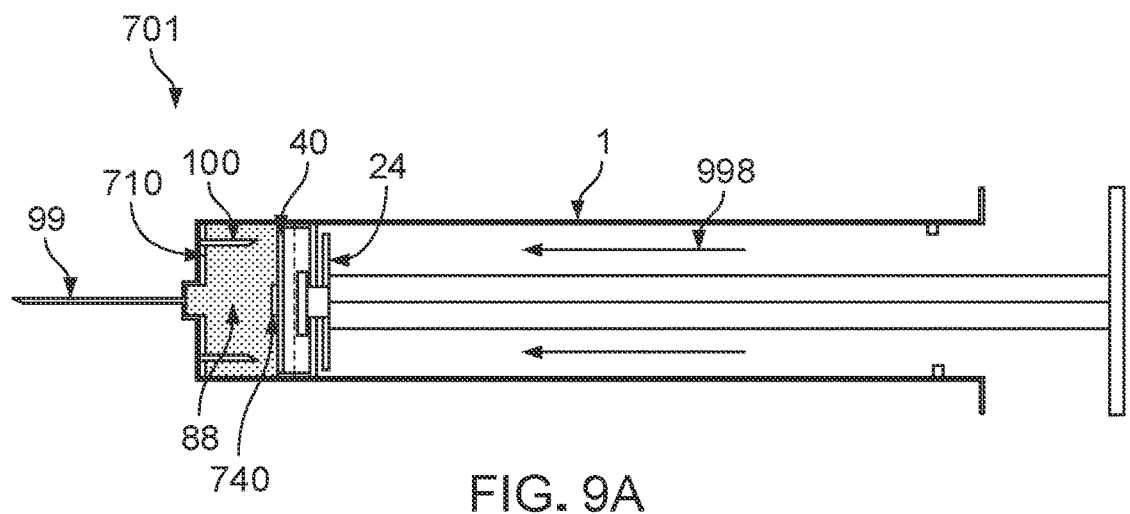
FIGS. 9A and 9B are illustrations of the operation of the mounting configuration of FIG. 7C.
Figure 9B:
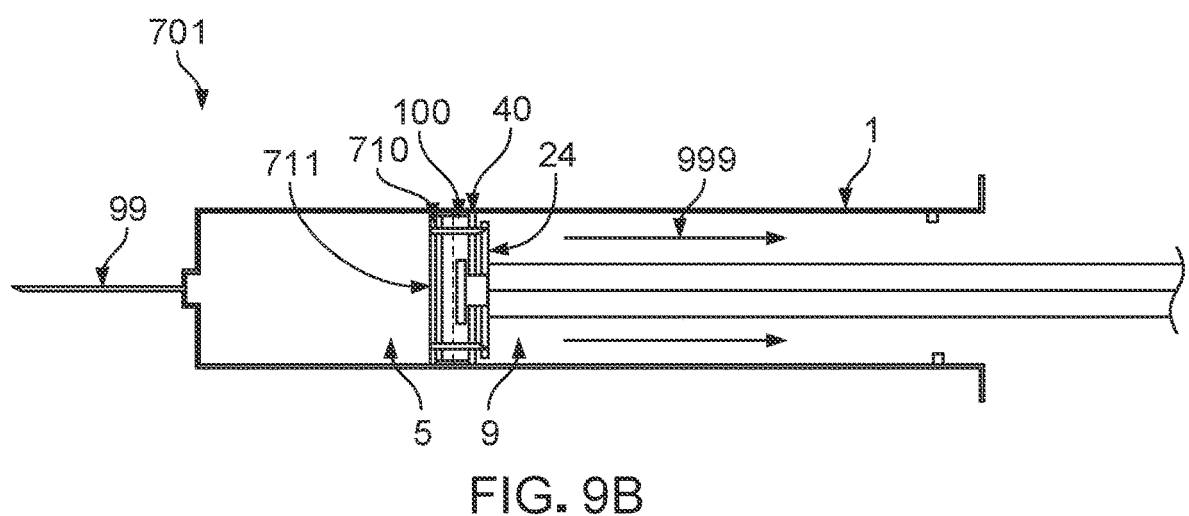

FIGS. 9A and 9B are illustrations of the operation of the mounting configuration of FIG. 7C. FIG. 9A shows the syringe assembly 701 of FIG. 7C having a medicament 88 in the distal enclosure 5 of the syringe 1, along with the mounting ring 710. In operation, the plunger 20 is driven distally (indicated by arrow 998) to drive the medicament 88 through the needle 99 until the distal surface 41 (shown in FIG. 1) of the plunger head seal 40 abuts the proximal face of the mounting ring 710 and the protrusion 740 mates with the central opening 741 (show in FIG. 7C) of the mounting ring 710, as shown in FIG. 9B. FIG. 9B shows a proximal movement (indicated by arrow 999) of the plunger 20 after a first injection operation. The piercing objects 100 are driven though the plunger head 40 and equalize the pressure between the distal enclosure 5 and the proximal region 9 as the plunger head 24 moves distally. In addition, the piercing objects 100 retain the mounting ring 710 against the plunger head seal 40.

Figure 10A:
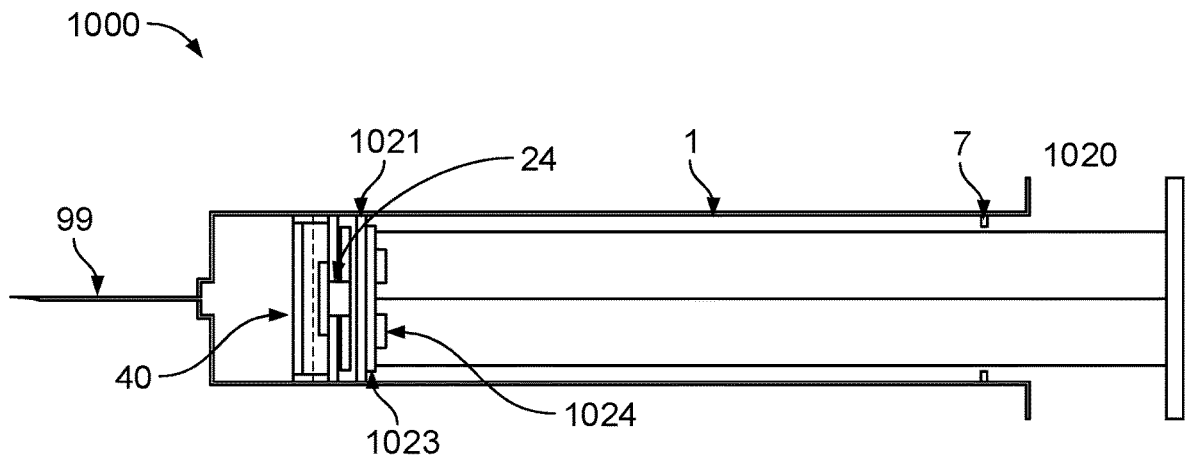
FIGS. 10A-E are illustrations of a detachable plunger stem design for use with a prefilled syringe.

FIGS. 10A-E are illustrations of a detachable plunger stem design for use with a pre-filed syringe. FIG. 10A shows a syringe assembly 1000 that includes a detachable plunger 1020 that provides single-use functionality to a disposable syringe when the disposable syringe is prefilled. The detachable plunger 1020 enables the plunger head 24 to be driven into the syringe body 1, but not withdrawn, because the detachable plunger 1020 is not securely mated with the plunger head 24 and can only apply an axial force in a single direction (e.g., distally, during a first injection operation). The syringe assembly 1000 includes the detachable plunger 1020 abutting a plunger head 24, with positioning fins 1024 of the plunger head rotationally coupling the detachable plunger 1020 to the plunger head 24. In some instances, the plunger head 24 does not include the positioning fins 1024, and the detachable plunger 1020 is free to rotate with respect to the plunger head 24. In some instances, and as shown, the detachable plunger 1020 also includes a gasket 1021 at the distal end to locate the detachable plunger 1020 in the syringe body 1, and, in some instances, to provide an interference fit between the detachable plunger 1020 and the syringe body 1 in order to prevent the detachable plunger 1020 from moving proximally in the syringe body 1 under its own weight.

Figure 10B:
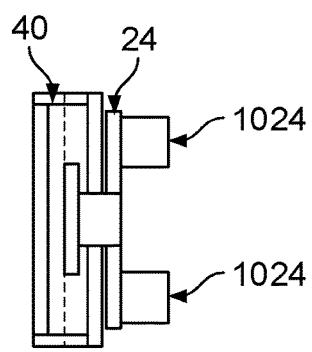
Figure 10C:
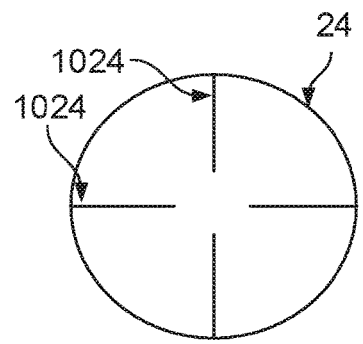
Figure 10D:
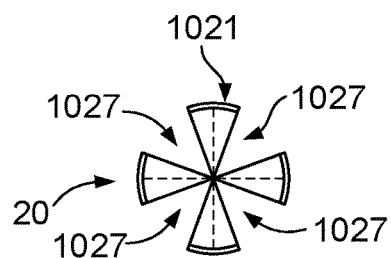
Figure 10E:
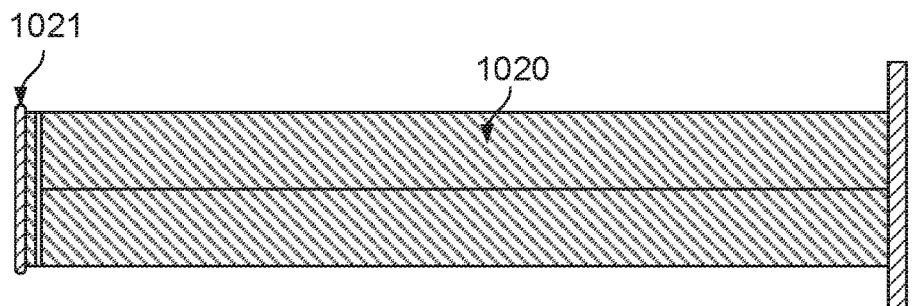

FIG. 10B shows a side cross-section view of the plunger head 24, with the plunger head seal 40 and the positioning fins 1024 extending proximally from the plunger head 24. FIG. 10C is a top view of the plunger head 24, showing the positioning fins 1024. FIGS. 10D and 10E are front and side views, respectively, of the detachable plunger 1020, showing the gasket 1021 disposed around the periphery of the distal end of the detachable plunger 1020. To rotationally couple the plunger head 24 and the detachable plunger 1020, in some instances, the distal end 1023 of the detachable plunger 1020, as shown in FIG. 10D, includes multiple grooves 1027. Fins 1024, which extend from the plunger head 24, are accommodated within grooves 1027, extending through the distal end 1023 of the detachable plunger 1020 and rotationally "locking" or coupling the plunger head 24 and the detachable plunger 1020. In some embodiments, the distal end 1023 of the detachable plunger 1020 has no grooves (e.g., the distal end 1023 of the detachable plunger 1020 is formed as a continuous circular disc), and plunger head 24 does not include fins 1024, so that the plunger head 24 and the detachable plunger 1020 are not rotationally coupled.

Figure 11A:
FIGS. 11A-C are illustrations of the operation of a prefilled syringe having the detachable plunger stem design of FIG. 10A.
Figure 11B:
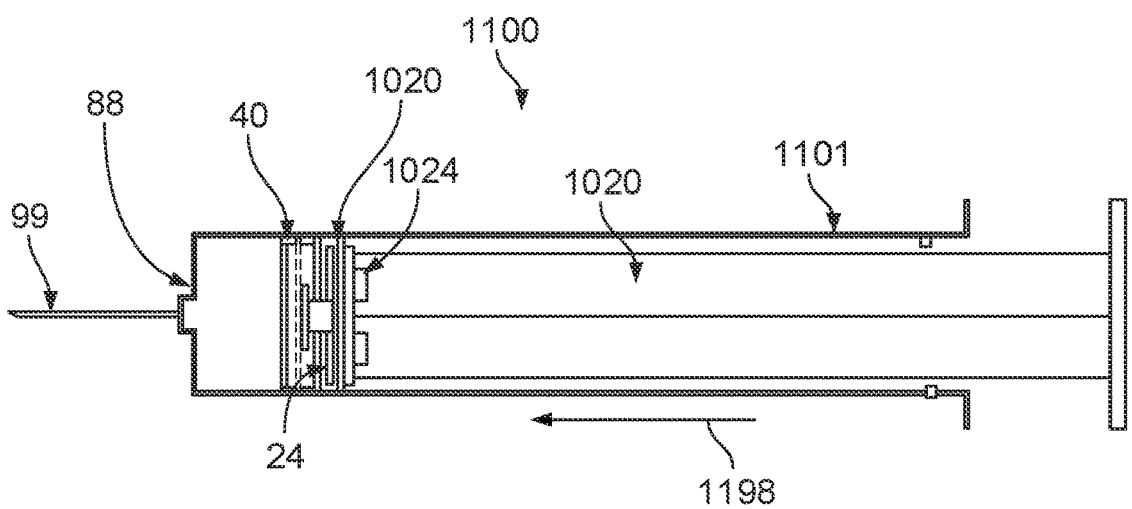
Figure 11C:
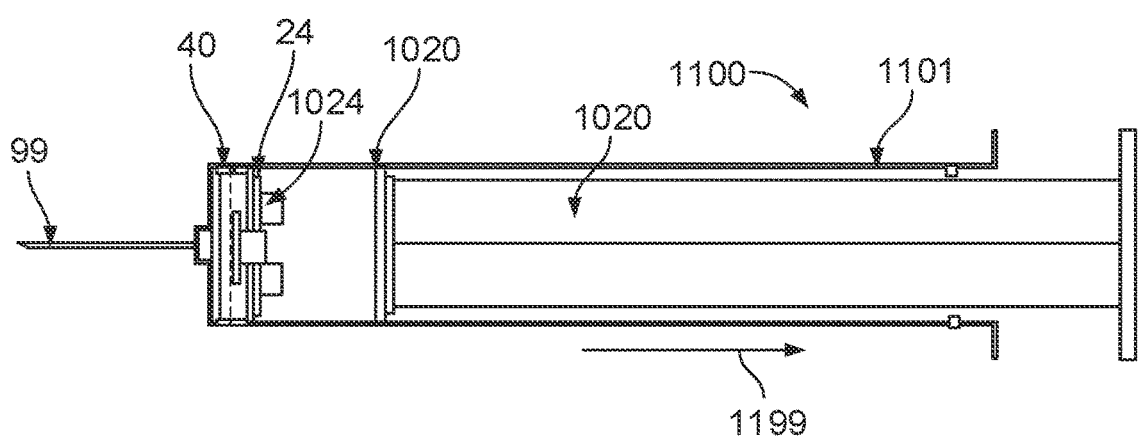

FIGS. 11A-C are illustrations of the operation of a prefilled syringe 1101 having the detachable plunger 1020 of FIG. 10A. FIG. 11A shows a prefilled syringe 1101 containing a medicament 88, with a needle 99 attached to the distal end and a plunger head 24 with positioning fins 1024 disposed at the proximal end of the prefilled syringe without a plunger attached. FIG. 11B shows a syringe assembly 1100, where a detachable plunger 1020 has driven (indicated by arrow 1198) the plunger head 24 distally into the prefilled syringe 1101 and driven a portion of the medicament 88 from the prefilled syringe 1101 though the needle 99 during a first injection operation. FIG. 11C shows the syringe assembly 1100 after the completion of the first injection operation, and with the detachable plunger 1020 being pulled proximally (indicated as arrow 1199) from the prefilled syringe 1101. The detachable plunger 1020 is separated from the plunger head 24 and the plunger head 24 is retained in the distal end of the prefilled syringe 1101, thus preventing a subsequent reuse of the syringe assembly 1100.

Figure 12A:
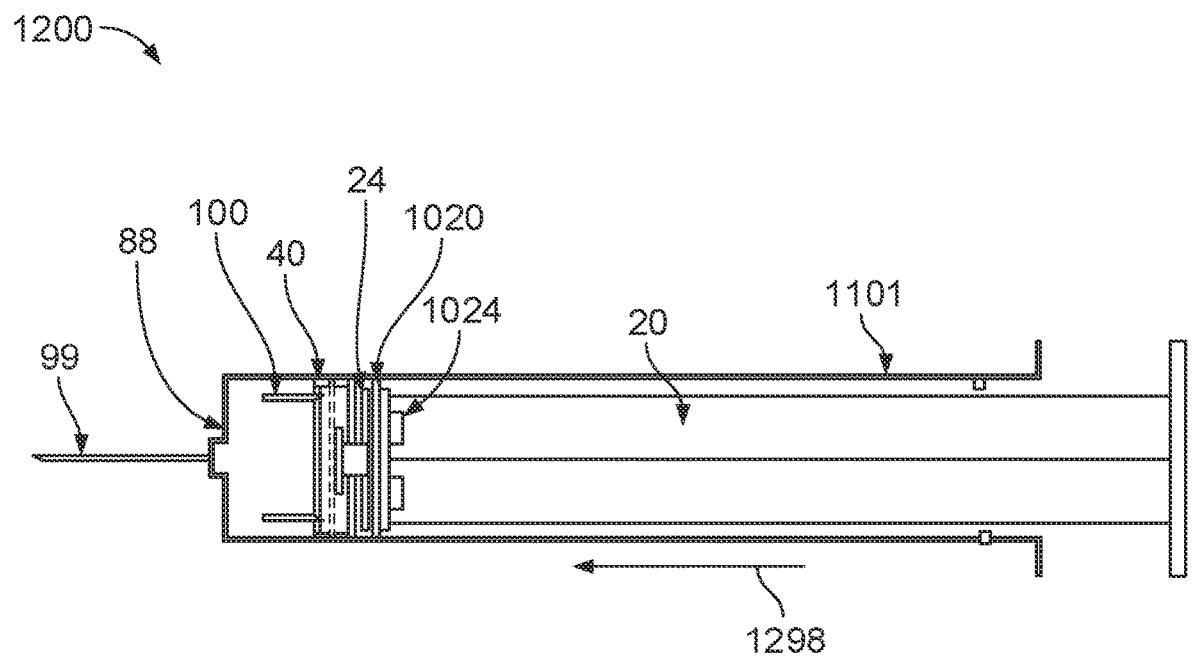
FIGS. 12A and 12B are illustrations of the operation of a prefilled syringe having the detachable plunger stem design of FIG. 10A with the pierceable objects configured to present re-use of the prefilled syringe.
Figure 12B:
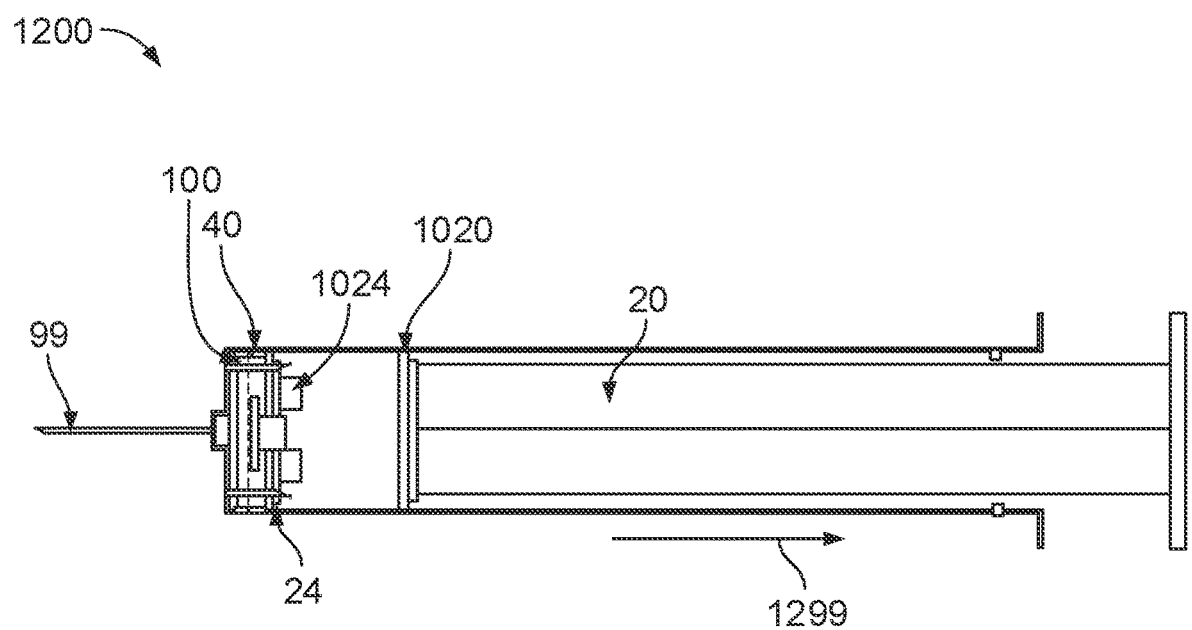

FIGS. 12A and 12B are illustrations of the operation of a prefilled syringe 1101 having the detachable plunger stem design of FIG. 10A with the pierceable objects configured to prevent re-use of the prefilled syringe. FIG. 12A shows a syringe assembly 1200 including a prefilled syringe 1101, a detachable plunger 1020, and a plunger head 24 with piercing objects 100 mounted in the plunger head seal 40. FIG. 12A is a combination of the detachable plunger system of FIGS. 10A-11C, with the re-use prevention mechanism of FIGS. 1-7A. FIG. 12A shows a first injection operation of the syringe assembly 1200, where a medicament 88 is driven from the prefilled syringe 1101 by distal movement of the plunger head seal 40 (indicated by arrow 1298). FIG. 12B shows the syringe assembly 1200 after the first injection operation is completed and the detachable plunger 1020 is moved proximally (indicated by arrow 1299) in the prefilled syringe 1101. The plunger head 24 was driven against the distal end of the prefilled syringe 1101 at the end of the first injection operation, and the piercing objects 100 were driven though the plunger head seal 40, as shown. The detachment of the detachable plunger 1020 from the plunger head 24 leaves the plunger head 24 at the distal end of the prefilled syringe 1101, where the plunger head seal 40 has been breached by the piercing objects 100. While FIGS. 12A and 12B show the syringe assembly 1200 using the re-use prevention mechanism of FIGS. 1-7A, in other instances, the syringe assembly includes the mounting ring 710 of FIGS. 7B and 7C.

The terms "drug" or "medicament" are used synonymously and describe a pharmaceutical formulation containing one or more active pharmaceutical ingredients or pharmaceutically acceptable salts or solvates thereof, and optionally a pharmaceutically acceptable carrier. An active pharmaceutical ingredient, in the broadest terms, is a chemical structure that has a biological effect on humans or animals. In pharmacology, a drug or medicament is used in the treatment, cure, prevention, or diagnosis of disease or used to otherwise enhance physical or mental well-being.

Those of skill in the art will understand that modifications (additions and/or removals) of various components of the apparatuses, methods, systems and embodiments described herein may be made without departing from the full scope and spirit of the present invention, which encompass such modifications and any and all equivalents thereof.

A number of implementations of the present disclosure have been described. Nevertheless, it will be understood that various modifications may be made without departing from the spirit and scope of the present disclosure. Accordingly, other implementations are within the scope of the following claims.

What is claimed is:

1. A single-use medical syringe comprising:
    a syringe body adapted to contain a medicament in an interior of the syringe body, the syringe body having a distal end adapted to deliver the medicament to a needle and an open proximal end; and
    a plunger assembly configured to be inserted into the open proximal end of the syringe body, the plunger assembly being movable with respect to the syringe body for driving the medicament from the syringe body through the needle, the plunger assembly comprising a proximal end adapted to be operated by a user of the single-use medical syringe and a distal end arranged to be driven to the distal end of the syringe body during an injection operation, the distal end of the plunger assembly comprising a plunger head adapted to sealingly engage an inner surface of the syringe body, the plunger head comprising:
        a sealing element arranged on a distal end of the plunger head to contact the medicament in the syringe body, and
        one or more hollow piercing elements disposed in the interior of the syringe body between a distal surface of the interior and the sealing element of the plunger head,
    wherein the one or more hollow piercing elements are arranged axially with respect to the syringe and positioned to be driven through the sealing element when the sealing element is driven against the distal end of the syringe body at the end of the injection operation;
    wherein, at the end of the injection operation, the one or more hollow piercing elements create a fluid passageway across the plunger head when the one or more hollow piercing elements pierce through the sealing element of the plunger head; and
    wherein the piercing ends of the one or more hollow piercing objects are disposed in the plunger head prior to the injection operation such that the one or more hollow piercing objects are carried by the plunger head, and wherein, during the injection operation, the blunt ends of the one or more hollow piercing objects contact the distal surface of the interior of the syringe body such that completion of the injection operation drives the piercing ends of the one or more hollow piercing objects through the sealing element of the plunger head to create the fluid passageway across the plunger head.

2. The single-use medical syringe of claim 1, wherein the one or more hollow piercing element comprise a piercing end and a blunt end opposite the piercing end and a hollow bore extending between the blunt end and the piercing end, wherein the piercing end is arranged closest to the sealing element, and wherein the blunt end is arranged closest to the distal surface, and wherein the hollow bore defines the fluid passageway across the plunger head when the one or more hollow piercing elements pierce through the sealing element of the plunger head.

3. The single-use medical syringe of claim 1, wherein the needle defines an internal cross-sectional bore area, and wherein a total internal cross-sectional bore area of the one or more hollow piercing objects is larger than the internal cross-sectional bore area of the needle.

4. The single-use medical syringe of claim 1, wherein the sealing element of the plunger head is constructed from an elastomeric sealing material.

5. The single-use medical syringe of claim 4, wherein the sealing element comprises a distal surface configured to contact the medicament and a proximal surface, wherein the plunger head comprises a rigid seal holding disc adjacent to the proximal surface of the sealing element.

6. The single-use medical syringe of claim 5, wherein the one or more piercing objects are sized and shaped to pierce through the sealing element, and the seal holding disc at the end of the injection operation to create the fluid passageway though the plunger head.

7. The single-use medical syringe of claim 5, wherein the seal holding disc defines one or more voids arranged to accept the one or more hollow piercing objects at the end of the injection operation.

8. A single-use medical syringe comprising:
    a syringe body adapted to contain a medicament in an interior of the syringe body, the syringe body having a distal end adapted to deliver the medicament to a needle and an open proximal end; and
    a plunger assembly configured to be inserted into the open proximal end of the syringe body, the plunger assembly being movable with respect to the syringe body for driving the medicament from the syringe body through the needle, the plunger assembly comprising a proximal end adapted to be operated by a user of the single-use medical syringe and a distal end arranged to be driven to the distal end of the syringe body during an injection operation, the distal end of the plunger assembly comprising a plunger head adapted to sealingly engage an inner surface of the syringe body, the plunger head comprising:

a sealing element arranged on a distal end of the plunger head to contact the medicament in the syringe body; and one or more hollow piercing elements disposed in the interior of the syringe body between a distal surface of the interior and the sealing element of the plunger head; and a mounting ring disposed in the interior of the syringe body and at the distal end of the interior of the syringe body, the mounting ring comprising a distal surface configured to abut the distal surface at distal end of the interior and a proximal surface configured to abut the sealing element at the end of the injection operation, wherein the one or more hollow piercing elements are arranged axially with respect to the syringe and positioned to be driven through the sealing element when the sealing element is driven against the distal end of the syringe body at the end of the injection operation;

wherein, at the end of the injection operation, the one or more hollow piercing elements create a fluid passageway across the plunger head when the one or more hollow piercing elements pierce through the sealing element of the plunger head; and wherein the one or more hollow piercing objects are carried by the mounting ring.

9. The single-use medical syringe of claim 8, wherein a proximal end of the plunger assembly comprises a plurality of positioning elements configured to rotationally couple the distal end of a plunger stem when the distal end of the plunger stem contacts the plunger head in the syringe body for driving the plunger head within the syringe body during the injection operation.

10. The single-use medical syringe of claim 9, wherein the plurality of positioning elements comprise positioning fins extending proximally from the plunger head.

11. The single-use medical syringe of claim 8, comprising a detachable plunger stem comprising:

a distal end configured to contact a proximal end of the plunger head and drive the plunger head within the syringe body during the injection operation without axially coupling to the plunger, and a proximal end configured to be operated by a user of the single-use medical syringe for applying a force to the plunger head.

12. The single-use medical syringe of claim 11, wherein a proximal end of the plunger assembly comprises a plurality of positioning elements configured to rotationally couple the distal end of the plunger stem when the distal end of the plunger stem contacts the plunger head in the syringe.

13. The single-use medical syringe of claim 12, wherein the distal end of the plunger stem defines a plurality of radial wedges, and wherein the plurality of positioning elements comprise positioning fins extending proximally from the plunger head and configured to extend into the radial wedges of the plunger stem when the distal end of the plunger stem contacts the proximal end of the plunger head.

14. The single-use medical syringe of claim 8, wherein the syringe body is configured to be disposed in a medical device having a drive mechanism for driving the plunger assembly into the syringe body.

15. The single-use medical syringe of claim 8, wherein the syringe body contains a medicament.

16. The single-use medical syringe of claim 8, wherein blunt ends of the one or more hollow piercing objects extend though the mounting ring such that hollow bores of the one or more hollow piercing objects are exposed at the distal surface of the mounting ring, and piercing ends of the one or more hollow piercing objects extend proximally towards the plunger head prior to the injection operation, wherein during the injection operation, the sealing element of the plunger head contacts the piercing ends of the one or more hollow piercing objects and completion of the injection operation drives the one or more hollow piercing objects through the sealing element to create the fluid passageway across the plunger head, and wherein the one or more hollow piercing objects retain the mounting ring to the plunger head at the completion of the injection operation.

17. The single-use medical syringe of claim 8, wherein the mounting ring comprises a central opening configured to allow the medicament to be driven from the distal end of the syringe body during the injection operation, and wherein the sealing element comprises a central protrusion extending distally, the central protrusion being sized and shaped to fit into the central opening of the mounting ring at the end of the injection operation.

* * * * *